(12) United States Patent
Bonaldo

(10) Patent No.: US 6,171,262 B1
(45) Date of Patent: Jan. 9, 2001

(54) RETRACTABLE BLOOD COLLECTION DEVICE

(75) Inventor: Jean M. Bonaldo, Upland, CA (US)

(73) Assignee: Creative Plastic Technology, LLC, Upland, CA (US)

(*) Notice: Under 35 U.S.C. 154(b), the term of this patent shall be extended for 0 days.

(21) Appl. No.: 09/372,479

(22) Filed: Aug. 11, 1999

(51) Int. Cl.[7] ............................. A61B 5/00; B65D 81/00
(52) U.S. Cl. .................................................. 600/573
(58) Field of Search ........................ 600/576, 578, 600/583

(56) References Cited

U.S. PATENT DOCUMENTS 5,069,225 * 12/1991 Okamura ............................ 600/578
5,423,758 * 6/1995 Shaw ................................. 600/576

* cited by examiner

*Primary Examiner*—Max Hindenburg
*Assistant Examiner*—Brian Szmal
(74) *Attorney, Agent, or Firm*—Roth & Goldman

(57) ABSTRACT

A retractable blood collection device having a housing comprised of relatively rotatable parts and a hub in the housing supporting a double ended cannula which is retracted by spring pressure into the housing when the housing parts are rotated to contain the used cannula in the housing for safe disposal.

23 Claims, 5 Drawing Sheets

RETRACTABLE BLOOD COLLECTION DEVICE

CROSS REFERENCE TO RELATED APPLICATIONS, IF ANY

None

BACKGROUND OF THE INVENTION AND PRIOR ART

The present invention relates to a medical apparatus for safely drawing blood or other fluid from a patient wherein the apparatus includes a cannula housing into which the cannula can be withdrawn and contained after use for safe disposal.

OBJECTS OF THE INVENTION

It is the primary object of the invention to provide a blood collection device in which the cannula may be automatically retracted into a housing by a spring after use merely by turning easily manipulatable rotatable parts of the housing to permit a non-circular portion of the cannula support to pass through a non-circular opening in an end of the housing to withdraw the cannula into the housing.

It is a further object of the invention to provide a reliable blood collection device comprised of a small number of parts, each of which are easily formed in mass production.

SUMMARY OF THE INVENTION

The present invention accordingly provides a retractable blood collection device comprising:

a) an elongated tubular housing having an end wall partially closing a first end of said housing;

b) a cannula support hub slidably supported in said housing for longitudinal movement therein;

c) a cannula affixed to and supported by said hub, said cannula having a first end extending from a first side of said hub exteriorly of said housing through said housing end wall, said cannula having a second end extending from a second side of said hub in said housing, said housing having a greater length than said cannula;

d) a cannula retainer ring rotatably affixed to said first end of said housing, said retainer ring having a centrally located aperture through which a portion of said hub and cannula protrude; and e) a compression spring in said housing seated between said hub and said first end of said housing biasing said hub for retracting said first end of said cannula into said housing to position said cannula completely in said housing.

DESCRIPTION OF THE PREFERRED EMBODIMENT

Figure 1:
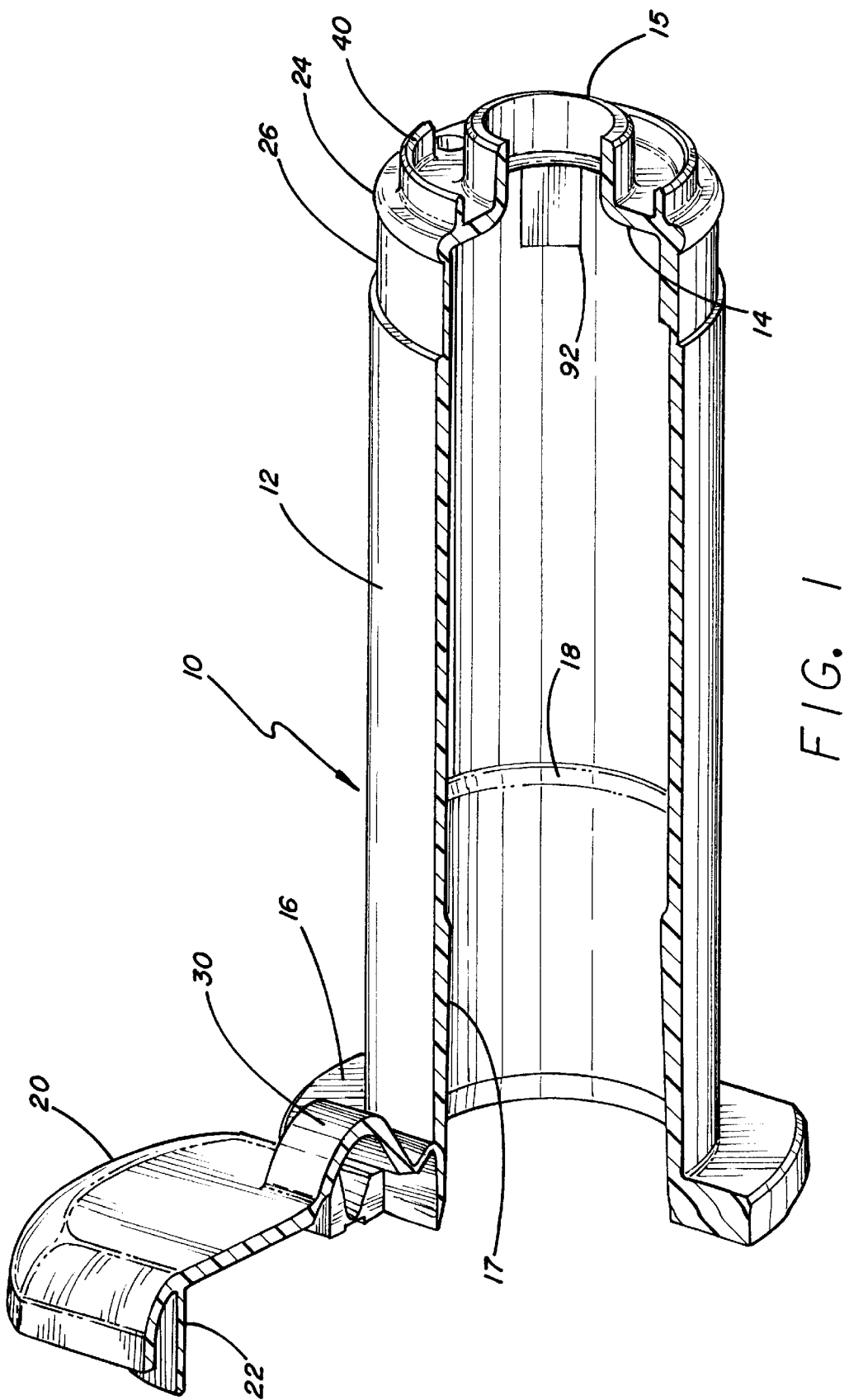
FIG. 1 is a perspective view of a housing for the blood collection device.
Figure 4:
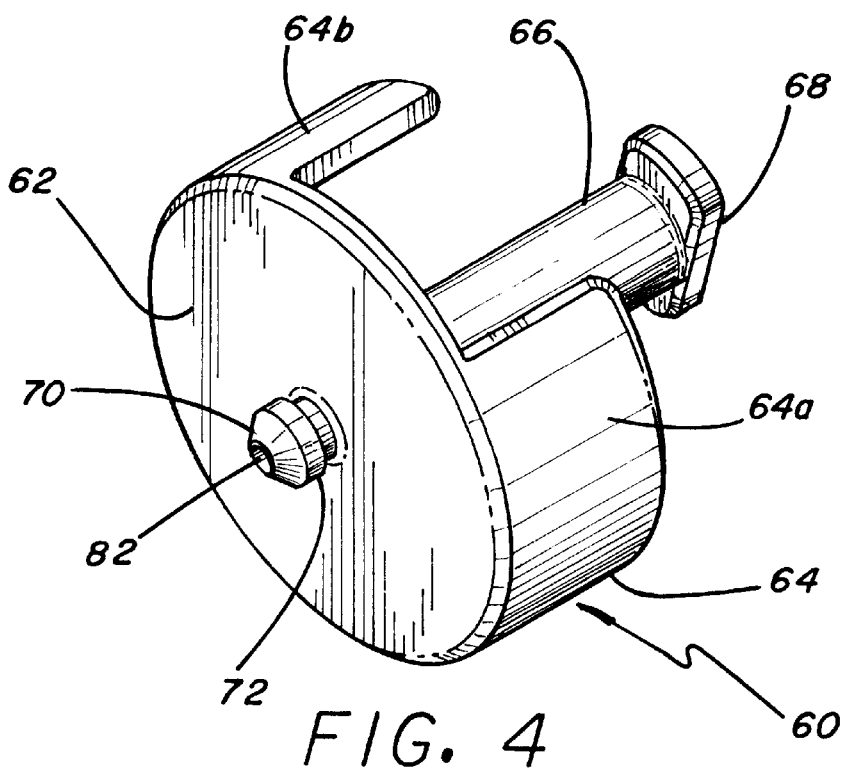
FIG. 4 is a perspective view of a cannula support hub.
Figure 5:
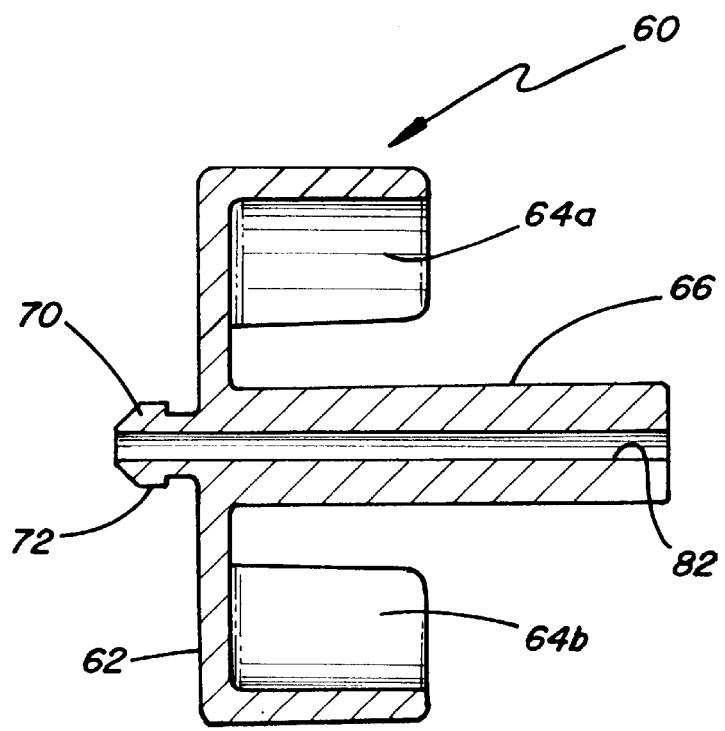
FIG. 5 is cross sectional plan view of the cannula support hub.
Figure 6:
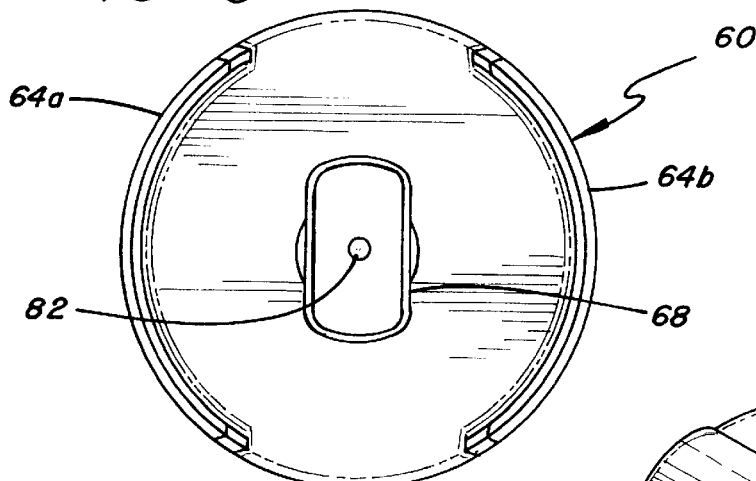
FIG. 6 is a right side elevation view of the cannula support hub.

FIG. 1 is a perspective view of an elongated generally cylindrical housing 10, preferably made of polypropylene plastic. The elongated tubular housing has a cylindrical side wall 12 and transversely extending end wall 14 which partially closes the right end of the housing as seen in the drawing. The left end of the housing 10 includes an integrally formed finger gripping collar 16 and plastic cover 20 connected to the housing by a hinge 30 of any suitable type, but preferably an integrally formed plastic hinge 30 which has elastic memory to bias the cover 20 to a position in which it ordinarily closes the open left end of the housing. The cover 20 also includes an integrally formed generally semi-circular guide skirt 22 on the inner side wall of the cover which is closely received in the interior of the preferably generally cylindrical wall 12 of the housing. The inherent elasticity of the materials of the cover and housing retain the cover in the closed position but permit easy opening thereof by finger pressure. As seen in FIG. 1, the longitudinally extending wall 12 of the housing is configured with a thickened section to provide a seat 18 of reduced diameter to prevent passage of a cannula support hub 60 (FIGS. 4–6) to the left past the seat.

Figure 3:
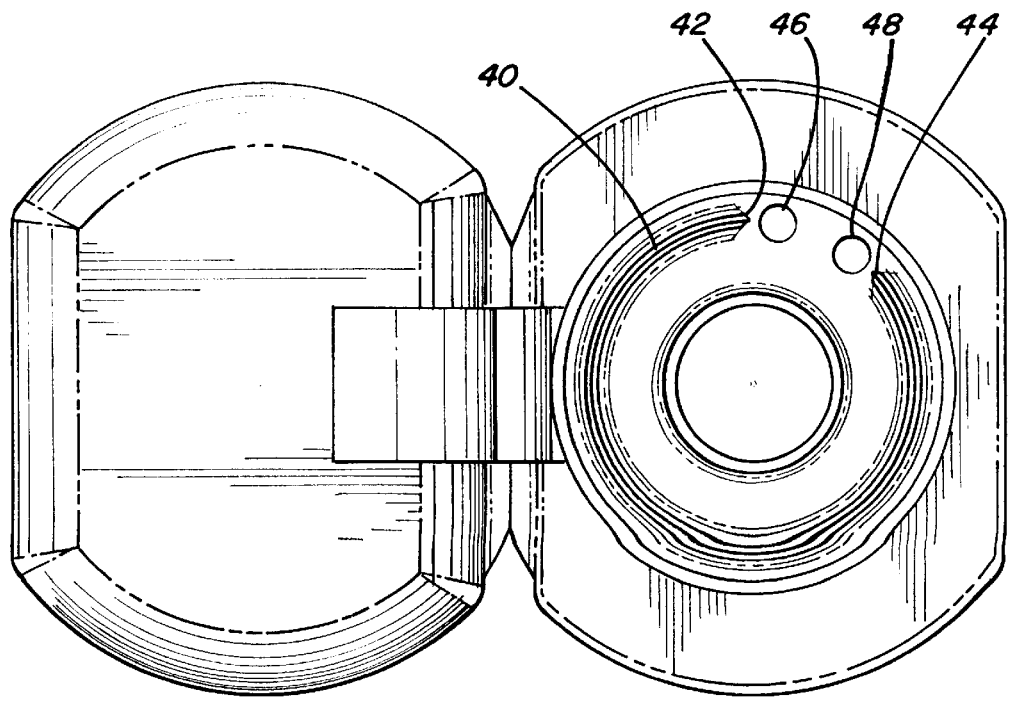
FIG. 3 is a right side elevation view of the housing.

FIGS. 1 and 3 illustrate the right end of the housing including the transversely disposed end wall 14 which terminates in an integrally formed axially extending cylindrical end 15 of reduced diameter. An annular rounded retainer enlargement 24 and a reduced diameter restraining groove 26 on the exterior of the cylindrical wall 12 of the housing mate with the interior wall of a retainer ring 50 to be described with reference to FIGS. 7 and 8 for holding the retainer ring on the end of the housing while permitting relative rotation between the retainer ring 50 and housing 10. The retainer ring 50 is preferably made of polypropylene plastic so that the retainer ring 50 can be elastically pressed onto the end of the housing to be retained thereon by the enlargement 24 and groove 26. Engageable rotation limit stops 42, 44, 52 are provided on the exterior surface of the end wall 14 of the housing and interior surface of the retainer ring 50 to limit relative rotation therebetween preferably to not exceed about 45° so that the ring 50 can easily be rotated manually relative to the housing 10 with one hand without having to shift the position of the user's hand. The rotation limit stops 42, 44 on the end of the housing can take any suitable form but, as shown, comprise the ends of an annular skirt 40 which are positioned for abutment with the rotation limit stop 52 on the retainer ring.

Figure 7:
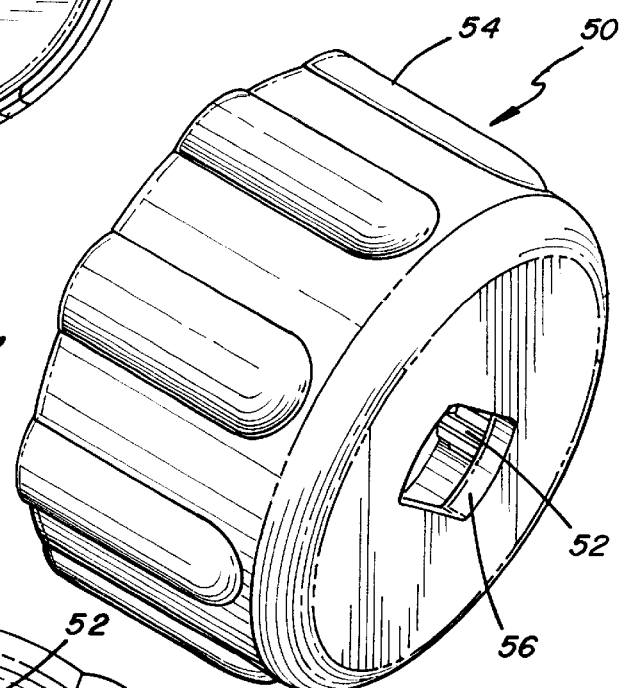
FIG. 7 is a perspective view of a cannula retainer ring.
Figure 8:
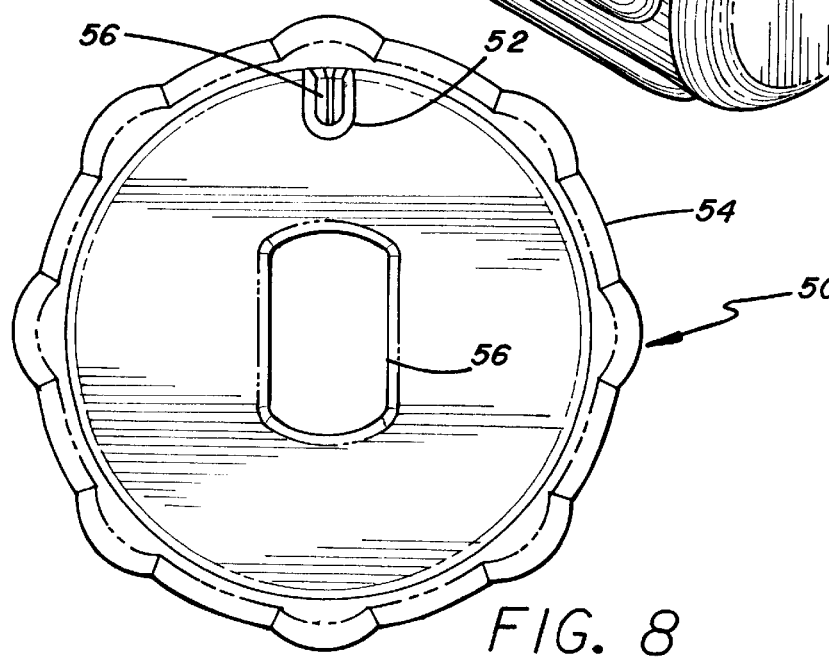
FIG. 8 is a left side elevation of the retainer ring.

In order to tactilely determine the relative position of the retainer ring 50 and housing 10, two circumfrentially spaced buttons or enlargements 46, 48 are provided on the outside of the end wall 14 of the housing positioned in the arc of the annular stop skirt 40 between the stops 42, 44 provided by the ends thereof. The rotation limit stop 52 on the retainer ring 50 is sized to snap into one or the other of the recesses between the limit stops 42, 44 and the enlargements 46, 48 to enable the user to feel whether the retainer ring is 50 in correct position relative to the housing 10. As seen in FIG. 7, the retainer ring is a generally cup shaped part having an exterior finger gripping surface 54 preferably formed by grooves or enlargements. As seen in FIG. 8, the retainer ring 50 has a non-circular central opening 56 which may take the shape of a rectangle, and the rotation limit stop 52 is integrally formed and extends radially inwardly from the side wall of the retainer ring to engage the stops 42, 44 provided by the ends of the annular skirt on the end wall of the housing 10. The stop 52 in the retainer ring 50 has an end surface 56 receivable in the spaces between the enlargements 46, 48 on the exterior surface of the end wall 14 of the housing and the stops 42, 44 provided by the ends of the annular housing skirt 40.

Figure 9:
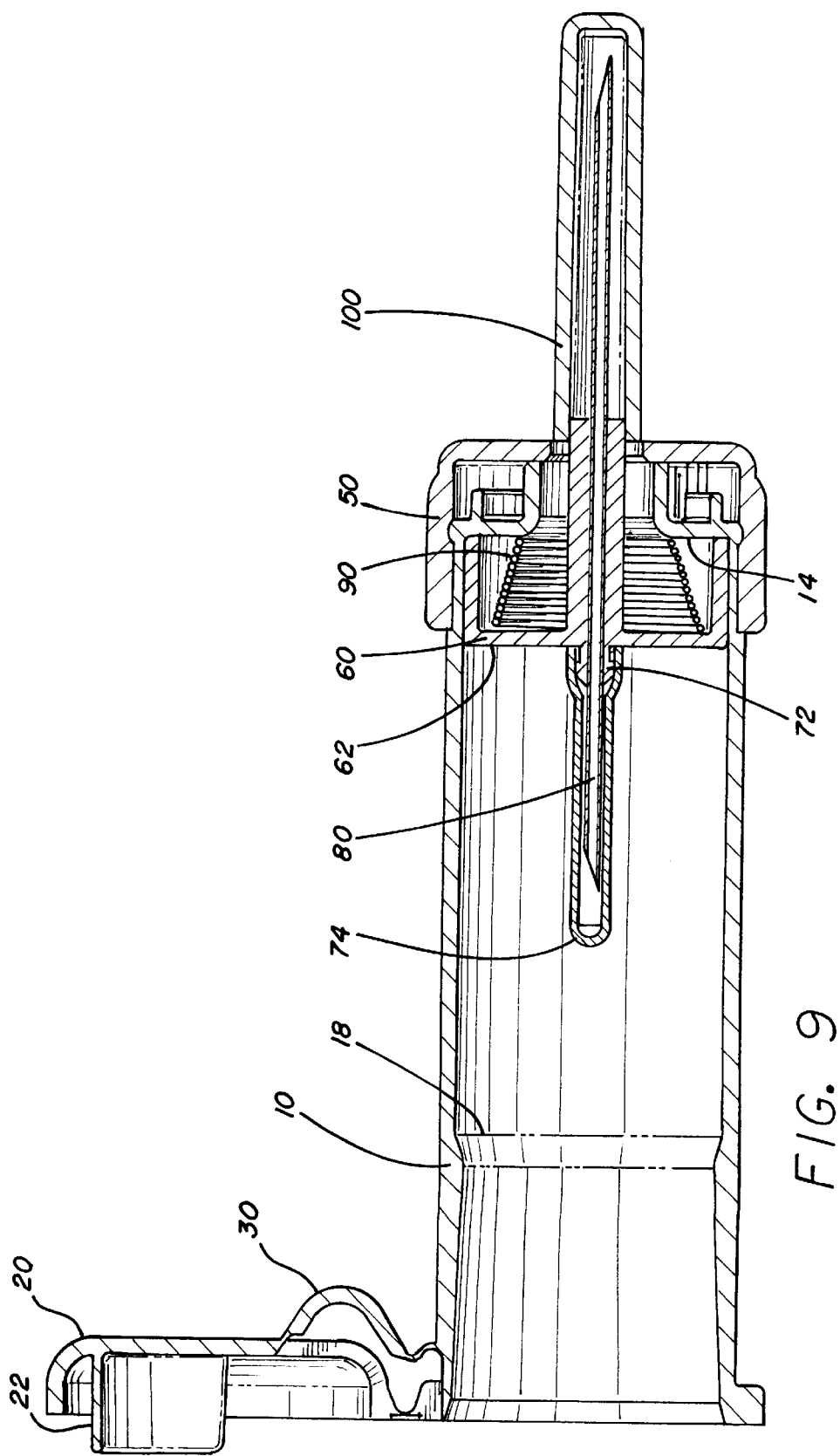
FIG. 9 is a longitudinal cross section of the assembled blood collection device.

A generally cup-shaped cannula support hub 60 (FIGS. 4–6), preferably also made of polypropolene plastic, is comprised of a transversely extending disk 62 and an axially extending skirt 64, preferably having two or more spaced annular sections 64a, 64b and a centrally located cannula support 66 having a non-circular portion 68, which for example may be rectangular or square, integrally formed on its end for passage through the opening 56 in the retainer ring 50. Preferably, the hub also includes an integrally formed retainer 70 having an enlarged lip 72 suitable for retaining a rubber or plastic protective boot 74 initially covering the left end of a double ended cannula 80 firmly supported in a centrally disposed passageway 82 which extends through the hub 60. The cannula 80 may be permanently attached in the cannula support 66 or the cannula passage in the support 66 may be threaded to receive a cannula of the user's choice. A permanently attached cannula will have one end which initially protrudes from the housing with the cannula 80 extending from each side of the hub 60 as seen in FIG. 9 which shows the assembled blood collection device. The centrally located non-circular opening 56 in the retainer ring 50 is sized to prevent passage of the non-circular end 68 of the cannula support 66 therethrough when the retainer ring 50 is in a first rotational position with respect to the hub 60 and housing 10 with the opening 56 permitting passage of the end 68 of the cannula support 66 therethrough when the retainer ring 50 is rotated to a second position with respect to the hub and housing.

A coil compression spring 90 (FIG. 9), preferably of stainless steel, is seated in the housing between the hub disc 62 and the transversely extending end wall 14 of the housing to bias the hub 60 and cannula 80 supported therein to the left so that the double ended cannula 80 is completely enclosed within the housing after use. The compression spring 90 may be cylindrical or, as shown, of generally conical shape and closely surrounds the elongated cannula support 66 to prevent mis-alignment of the hub 60 as it longitudinally slides in the housing 10 to its engagement with the seat 18 where continued leftward motion of the hub and supported cannula is terminated.

Figure 2:
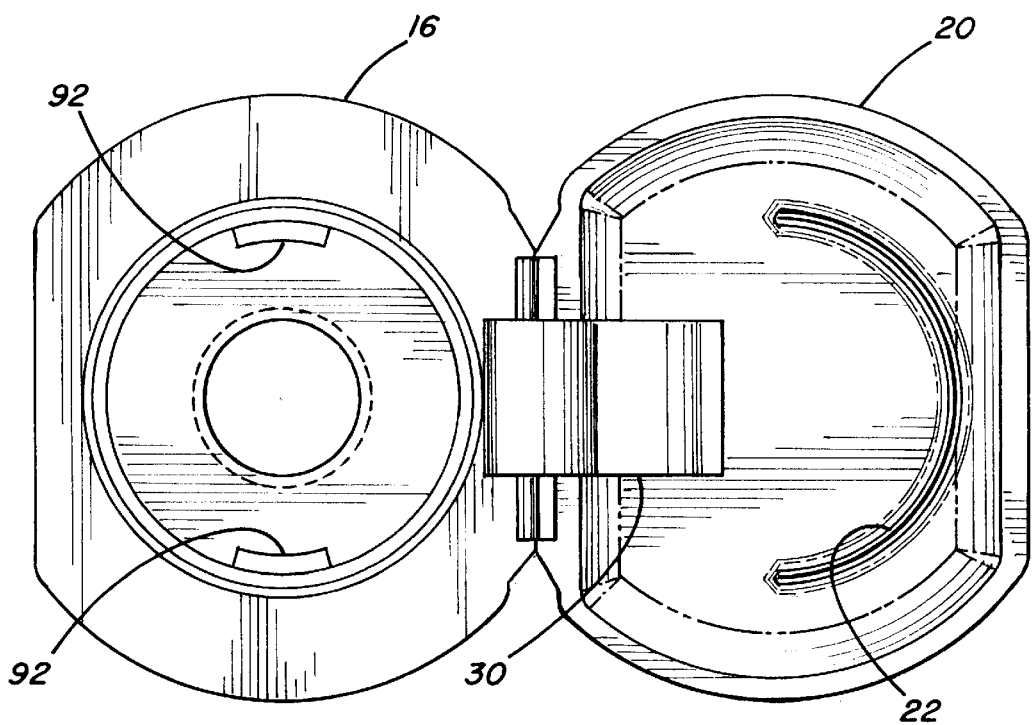
FIG. 2 is a left side elevation view of the housing showing the end cover.

The spaces between the annular skirt portions 64a, 64b of the hub conveniently form keyways for receiving longitudinally extending keys 92 integrally formed on the interior cylindrical wall of the housing as seen in FIGS. 1 and 2 to guide the hub 60 in its sliding movement in the housing and prevent relative rotation therebetween.

The assembled device preferably also is shipped with a protective sheath 100 of rubber, plastic or otherwise elastically stretchable material for covering the projecting end of the cannula 80 prior to use. The sheath is frictionally retained on the non-circular end 68 of the cannula support which essentially comprises a lip for elastically retaining the sheath.

In operation, the elastic boot 74 or cover over the interior end of the double ended cannula 80 is first removed then a suitable blood collection container having a piercable end is inserted into the open end of the housing where it is pierced by the inner end of the cannula 80. The outer protective sheath 100 covering the cannula is then removed, the blood collection device used in its intended fashion, and, after drawing of the blood sample, the cannula 80 is removed from the patient's vein. The retainer ring 50 is then easily rotated, preferably clockwise, relative to the housing with one hand through its path of travel to permit the non-circular end 68 of the cannula support hub to align with the non-circular opening 56 in the retainer ring 50 to permit the spring 90 to passively withdraw the end 68 of the cannula support hub and the cannula 80 completely into the housing 10 for safe disposal.

While the foregoing constitutes a complete description of the preferred embodiment, it will be appreciated by persons skilled in the art that modifications can be made from the preferred embodiment and the scope of protection is defined by the following claims.

What is claimed is:

1. A retractable blood collection device comprising:
   a) an elongated tubular housing having an end wall partially closing a first end of said housing;
   b) a cannula support hub slidably supported in said housing for longitudinal movement therein, said hub and said housing having at least one mating key and keyway for preventing rotation of said hub relative to said housing proximate said first end of said housing, said hub further including an axially extending cannula support having at least a portion of non-circular cross-section on a first side of said hub which, during use, extends exteriorly of said housing proximate said first end of said housing;
   c) a cannula affixed to and supported by said hub, said cannula having a first end which, during use, extends with said cannula support portion of non-circular cross-section exteriorly of said housing through said housing end wall, said cannula having a second end extending from a second side of said hub in said housing, said housing having a greater length than said cannula;
   d) a cannula retainer ring rotatably affixed to said first end of said housing, said retainer ring having a centrally located aperture through which said non-circular portion of said support on said hub and cannula protrude during use, said aperture in said retainer ring being of non-circular cross section and being sized to prevent passage of said non-circular portion of said cannula support therethrough when said retainer ring is in a first rotational position during use of said cannula with respect to said hub, said aperture permitting passage of said non-circular portion of said cannula support therethrough when said retainer ring is in a second rotational position with respect to said hub to retract said cannula into said housing; and
   e) a compression spring in said housing seated between said hub and said first end of said housing biasing said hub to retract said non-circular portion of said hub and said first end of said cannula into said housing when said retainer ring is rotated to said second rotational postion relative to said housing to position said cannula completely in said housing after use.

2. The blood collection device of claim 1, further comprising a gripping collar integrally formed with said housing at an open second end of said housing.

3. The blood collection device of claim 2, further comprising a cover for closing said open second end of said housing, said cover being attached to said housing by a hinge.

4. The blood collection device of claim 3, wherein said housing is plastic and said cover and hinge are integrally formed with said housing, said hinge having elastic memory to bias said cover to a closed position.

5. The blood collection device of claim 2, further comprising a seat internally formed in said housing for limiting movement of said hub and cannula toward said open second end of said housing and said housing and hub having a mating longitudinally extending key and keyway for preventing rotation of said hub in said housing.

6. The blood collection device of claim 5, wherein said retainer ring is plastic and further comprising a mating annular enlargement and annular recess for retaining said retainer ring on said housing while permitting relative rotation therebetween.

7. The blood collection device of claim 6, wherein said mating enlargement and recess comprise an annular enlargement and an annular retainer ring restraining groove on an exterior surface of said housing proximate said first end of said housing, and an internal groove on said retainer ring receiving said enlargement, said ring being elastically retained on said housing.

8. The blood collection device of claim 6, further comprising engageable rotation limit stops on said retainer ring and said housing for limiting relative rotation between said retainer ring and housing.

9. The blood collection device of claim 8, wherein said stops comprise a stop having a radial extent on an interior surface of said retainer ring and annularly spaced stops having a radial extent on an exterior surface of said housing, abutment of said radial extents of said stops limiting relative rotation of said housing and said retainer ring.

10. The blood collection device of claim 9, wherein said stops limit relative rotation of said housing and retainer ring to not exceed 45 degrees.

11. The blood collection device of claim 10, further comprising mating tactile position determiners each having an axial extent on said housing and said retainer ring.

12. The blood collection device of claim 11, wherein said position determiners comprise circumfrentially spaced enlargements on an exterior end surface of said housing and a transversely extending surface of said stop on said retainer ring, said enlargements being located between said stops on said housing.

13. The blood collection device of claim 9, wherein said hub comprises a cup shaped member having a bottom and an annular support surface engageable with an interior annular surface of said housing.

14. The blood collection device of claim 13, wherein said hub is plastic and said annular support surface has circumfrentially spaced support portions.

15. The blood collection device of claim 14, having two of said circumfrentially spaced support portions, said support portions defining two of said keyways therebetween, said housing having two of said mating keys therein which mate with said keyways.

16. The blood collection device of claim 13, wherein said portion of non-circular cross-section of said cannula support centrally extends from said bottom of said cup shaped member.

17. The blood collection device of claim 16, wherein said portion of non-circular cross section is located at an end of said cannula support.

18. The blood collection device of claim 13, wherein said hub further comprises a cannula boot retainer integrally formed with and extending from said bottom of said cup shaped member toward said second end of said housing and a protective boot affixed to said boot retainer and covering said second end of said cannula.

19. The blood collection device of claim 1, further comprising a removeable protective sheath for covering said first end of said cannula projecting from said first end of said housing, said portion of non-circular cross section of said cannula support comprising a lip for elastically retaining said sheath.

20. The blood collection device of claim 19, wherein said sheath, said portion of non-circular cross-section of said cannula support and said aperture in said retainer ring are of generally rectangular cross-section.

21. The blood collection device of claim 20, wherein said cross-section is substantially square.

22. The blood collection device of claim 1, wherein said spring is a coil spring of stainless steel.

23. The blood collection device of claim 1, wherein said housing, said hub and said retainer ring are formed of medical grade polypropylene.

* * * * *